US008980932B2

(12) United States Patent
Lambin et al.

(10) Patent No.: US 8,980,932 B2
(45) Date of Patent: Mar. 17, 2015

(54) CANCER TARGETING USING CARBONIC ANHYDRASE ISOFORM IX INHIBITORS

(75) Inventors: Philippe Lambin, Genappe Bousvalle (BE); Jean-Yves Winum, Saint Andre de Sangonis (FR); Claudiu Supuran, Florence (IT)

(73) Assignees: Stichting Maastricht Radiation Oncology "Maastro-Clinic", Maastricht (NL); Université Montpellier 2 Sciences et Techniques, Montpellier (FR); Claudiu Supuran, Florence (IT)

( * ) Notice: Subject to any disclaimer, the term of this patent is extended or adjusted under 35 U.S.C. 154(b) by 0 days.

(21) Appl. No.: 13/997,378

(22) PCT Filed: Dec. 21, 2011

(86) PCT No.: PCT/NL2011/000083
§ 371 (c)(1),
(2), (4) Date: Jun. 24, 2013

(87) PCT Pub. No.: WO2012/087115
PCT Pub. Date: Jun. 28, 2012

(65) Prior Publication Data
US 2013/0274305 A1 Oct. 17, 2013

(30) Foreign Application Priority Data
Dec. 24, 2010 (NL) ...................................... 1038473

(51) Int. Cl.
*C07D 233/95* (2006.01)
*C07D 233/88* (2006.01)
*C07D 233/91* (2006.01)

(52) U.S. Cl.
CPC ............ *C07D 233/95* (2013.01); *C07D 233/88* (2013.01); *C07D 233/91* (2013.01)
USPC ...................... 514/398; 548/326.5; 548/327.1

(58) Field of Classification Search
USPC ...................................................... 548/327.1
See application file for complete search history.

(56) References Cited

U.S. PATENT DOCUMENTS 3,683,949 A * 8/1972 Perkins ........................... 137/84
8,236,843 B2 * 8/2012 Sakhardande et al. ........ 514/398

FOREIGN PATENT DOCUMENTS

| CA | 986511 A1 * | 3/1976 |
| WO | WO 2001/19799 A2 | 3/2001 |
| WO | WO 2004/048544 A2 | 6/2004 |
| WO | WO 2006/102759 A1 | 10/2006 |
| WO | WO 2006/137092 A1 | 12/2006 |
| WO | WO 2008/071421 A1 | 6/2008 |
| WO | WO 2009/070045 A2 | 6/2009 |
| WO | WO 2009/089383 A2 | 7/2009 |

OTHER PUBLICATIONS

Brizel et al., "Elevated Tumor Lactate Concentrations Predict for an Increased Risk of Metastases in Head-and-Neck Cancer," *Int. J. Radiat. Oncol. Biol. Phys.*, 51, pp. 349-353 (2001).
Dubois et al., "Imaging the Hypoxia Surrogate Marker CA IX Requires Expression and Catalytic Activity for Binding Fluorescent Sulfonamide Inhibitors," *Radiotherapy and Oncology*, 83, pp. 367-373 (2007).
Ganguly et al., "Synthesis and Screening of N-(Aryl)(-2-)2-Methyl-4-Nitro-1H-Imidazol-1-YL-) Acetamides for Antibacterial Activity," *J. Institution of Chemists*, 79(6), pp. 178-181 (2007).
Khalifah, Raja G., "The Carbon Dioxide Hydration Activity of Carbonic Anhydrase," *J. Biol. Chem.*, 246(8), pp. 2561-2573 (Apr. 25, 1971).
Melillo, Giovanni, "Inhibiting Hypoxia-Inducible Factor 1 for Cancer Therapy," *Mol Cancer Res.*, 4(9), pp. 601-605 (Sep. 2006).
Overgaard Jens, "Sensitization of Hypoxic Tumour Cells—Clinical Experience," *Int. J. Radiat. Biol.*, 56(5), pp. 801-811 (Nov. 1989).
Overgaard et al., "A Randomized Double-Blind Phase III Study of Nimorazole as a Hypoxic Radiosensitizer of Primary Radiotherapy in Supraglottic Larynx and Pharynx Carcinoma," *Radiotherapy and Oncology*, 46(2), pp. 135-146 (Feb. 1998).
Pastorekova et al., "A Novel Quasi-Viral Agent, MaTu, is a Two-Component System," *Virology*, 187, pp. 620-626 (1992).
Quennet et al., "Tumor Lactate Content Predicts for Response to Fractionated Irradiation of Human Squamous Cell Carcinomas in Nude Mice," *Radiotherapy and Oncology*, 81(2), pp. 130-135 (Nov. 2006).
Supuran, Claudiu T., "Carbonic Anhydrases: Novel Therapeutic Applications for Inhibitors and Activators," *Nat. Rev. Drug Discov.*, 7(2), pp. 168-181 (Feb. 2008).
Svastová et al., "Hypoxia Activates the Capacity of Tumor-Associated Carbonic Anhydrase IX to Acidify Extracellular pH," *FEBS Lett.*, 577(3), pp. 439-445 (Nov. 2004).
Thomlinson et al., "The Histological Structure of Some Human Lung Cancers and the Possible Implications for Radiotherapy," *Br. J. Cancer*, 9(4), pp. 539-549 (Dec. 1955).
Winum et al., "Inhibition of Carbonic Anhydrase IX: A New Strategy Against Cancer," *Anti-Cancer Agents Med. Chem.*, 9(6), pp. 693-702 (Jul. 2009).
EPO, International Search Report in International Patent Application No. PCT/NL2011/00083, 3 pp. (Mar. 3, 2012).

* cited by examiner

*Primary Examiner* — Joseph Kosack
*Assistant Examiner* — Amanda L Aguirre
(74) *Attorney, Agent, or Firm* — Leydig, Voit & Mayer, Ltd.

(57) ABSTRACT

The present invention concerns novel carbonic anhydrase IX inhibitors comprising a nitroimidazole moiety and their use in therapy of hypoxic conditions, in particular cancer treatment, especially chemotherapy and radiotherapy. The compounds of the invention have an increased specificity for the carbonic anhydrase IX enzyme compared to the art. The present invention relates to novel nitroimidazole derivates represented by formula (1).

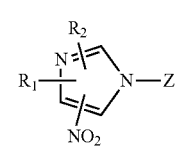

Formula (1)

13 Claims, 9 Drawing Sheets

Scheme 1:

Figure 1

Scheme 2:

CANCER TARGETING USING CARBONIC ANHYDRASE ISOFORM IX INHIBITORS

CROSS-REFERENCE TO RELATED APPLICATIONS

This patent application is the U.S. national phase of International Application No. PCT/NL2011/000083, filed Dec. 21, 2011, which claims the benefit of Dutch Patent Application No. NL 1038473, filed Dec. 24, 2010; the disclosures of the '083 and the '473 application are incorporated by reference.

FIELD OF THE INVENTION

The present invention concerns novel carbonic anhydrase IX inhibitors comprising a nitroimidazole moiety including their use in cancer treatment, especially radiotherapy.

BACKGROUND

Cancer is a leading cause of death and accounts for approximately 13% of all deaths in the world. Most cancers form solid tumors in tissues like head and neck, colon, breast, lung, liver and stomach, and are often characterized by low oxygen concentrations (hypoxia) and acidification of the microenvironment surrounding the tumor cells. Hypoxia and acidification of the extratumoral environment are both associated with aggressive tumor growth, metastasis formation and poor response to radiotherapy, surgery and/or to anticancer chemotherapy. The most important pathway that acts on changes in oxygen concentration is the 'Hypoxia Inducible Factor-1 pathway' (HIF-1 pathway). Under hypoxic conditions, the transcription factor HIF-1α is stabilized and binds to HIF-1β. The formed complex can translocate to the nucleus and bind to the hypoxic-responsive elements (HRE's) of genes involved in anaerobic metabolism, pH regulation, angiogenesis, cell proliferation and survival.

Carbonic anhydrases (CAs) form a large family of ubiquitous zinc metalloenzymes of great physiological importance. As catalysts of reversible hydration of carbon dioxide to bicarbonate and protons ($CO_2 + H_2O \Leftrightarrow H^+ + HCO_3^-$), these enzymes participate in a variety of biological processes, including respiration, calcification, acid-base balance, bone resorption, formation of aqueous humor. To date, 16 isozymes are characterized from which 15 present in humans. CAs in humans are present in several tissues (e.g. GI tract, reproductive tract, skin, kidneys, lungs, eyes, . . . ) and are localized in different parts of the cell. Basically, there are several cytosolic forms (CA I-III, CA VII), four membrane-bound isozymes (CA IV, CA IX, CA XII and CA XIV), one mitochondrial form (CA V) as well as a secreted CA isozyme, CA VI.

It has been shown that some tumor cells predominantly express only some membrane-associated CA isozymes, such as CA IX and CA XII. CAs show considerable diversity in their tissue distribution, levels, and putative or established biological functions. Some of the CAs are expressed in almost all tissues (CA II), whereas the expression of others appears to be more restricted (e.g., CA VI and CA VII in salivary glands).

Furthermore, it is conceivable that CA activity might also be well exploited in tumors, since tumors often display a reversed pH gradient across the plasma membrane when compared with normal tissues, indicating the contribution of CAs in providing protons for acidification of the extracellular environment and bicarbonate ions to maintain a neutral intracellular milieu. In addition to the acidifying effect on the extracellular pH, it can influence the uptake of anticancer drugs and modulate the response of tumor cells to conventional therapy, such as radiation therapy. One of the CA isozymes, CA IX, shows restricted expression in normal tissues, but is tightly associated with different types of tumors. CA IX, originally detected in human carcinoma HeLa cells as a cell density-regulated antigen (Pastorekova et al, 1992), is strongly induced by tumor hypoxia, through a transcriptional activation by the HIF-1 pathway. Strong association between carbonic anhydrase CA IX expression and intratumoral hypoxia has been demonstrated in carcinomas. CA IX distribution is often examined in relation to the extent of necrosis as an indicator of severe hypoxia and to microvascular density as a measure of angiogenesis. Furthermore, CA IX associated with worse relapse-free survival and overall survival in patients with invasive tumors. CA IX is also a significant prognostic indicator of overall survival and metastasis-free survival after radiotherapy and chemoradiotherapy.

Hypoxia is linked with acidification of extracellular environment that facilitates tumor invasion and CA IX is believed to play a role in this process via its catalytic activity (Svastova et al, 2004). CA IX has a very high catalytic activity with the highest proton transfer rate among the known CAs, has been shown to acidify the extracellular environment and is therefore an interesting target for anticancer therapy, preferably in combination with conventional treatment schedules. Targeting CA IX would be preferred above targeting HIF-1, the master regulator of the transcriptional response of mammalian cells to oxygen deprivation, since controversial results have been reported depending on the cell type used, the subunit targeted, the site of tumor and the timing of HIF-1 inhibition (early or later in tumor growth). Furthermore, because most of the small-molecules inhibitors of HIF-1 affect multiple signalling pathways and/or targets indirectly associated with HIF, assessment of their activity as HIF inhibitors cannot be based on therapeutic efficacy, which might be unrelated to HIF inhibition (Melillo, 2006).

Recently, it has emerged that carbonic anhydrase inhibitors (CAIs) could have potential, besides the established role as diuretics and anti-glaucoma drugs, as novel anti-obesity, anti-cancer and anti-infective drugs. There are 2 main classes of carbonic anhydrase inhibitors: the metal complexing anions and the unsubstituted sulfonamides and their derivatives, which bind to the Zinc ion of the enzyme either by substituting the nonprotein zinc ligand or add to the metal coordination sphere (Supuran, 2008). However, the critical problem in designing these inhibitors is the high number of isozymes, the diffuse localization in tissues and the lack of isozyme selectivity of the presently available inhibitors.

All six classical CAIs (acetazolamide, methazolamide, ethoxzolamide, dichlorophenamide, dorzolamide, and dichlorophenamide) used in clinical medicine or as diagnostic tools, show some tumor growth inhibitory properties. Most of the clinically used sulfonamides mentioned above are systemically acting inhibitors showing several undesired side effects due to inhibition of many of the different CA isozymes present in the target tissue/organ (15 isoforms are presently known in humans). Therefore, many attempts to design and synthesize new sulfonamides were recently reported, in order to avoid such side effects. Isozymes associated to cell membranes (CA IV, CA IX, CA XII and CA XIV), with the enzyme active site generally oriented extracellularly, provide a rational basis for targeting. CA IX and CA XII are both extracellularly located on hypoxic tumor cells and are therefore the best candidates.

The ideal characteristics for specific CA IX inhibitors should demonstrate a relatively low inhibition constant (Ki in the nanomolar range) and should be relatively specific over the cytosolic enzymes CA I and CA II. A number of aromatic sulfonamides has been presented (see e.g. WO02004048544) that specifically bind to the extracellular components of the in particular CAIX enzyme, which show a higher specificity than those hitherto known in the art. Therapeutic and diagnostic sulfonamide agents are described in WO2006137092. In WO2008071421 it was shown that the inhibitory effect of heterocyclic sulfonamides can be further increased by oxidative substituents, in particular nitrosated or nitrosylated substituents, since such groups may increase the acidity of the zinc binding groups and as such being beneficial for the carbonic anhydrase inhibitory properties. Sulfonamide-based metal chelate complexes for imaging are described in WO2009089383. However, a large variation is reported in CA IX inhibitory constants for the sulfonamides as well as variation in the selectivity of the inhibitors. Sulfamate and sulfamide inhibitors have also been proposed as candidates (Winum et al, 2009).

Traditional anticancer therapy like surgery, irradiation and chemotherapy are used to treat cancer patients as a combined or single treatment. The basic principle of irradiation is to damage the cancer cells to such an extent that they will die. Free radicals are formed and damage the DNA immediately or they react with oxygen, creating reactive oxygen species which damage the cell and more specific the DNA in the cell. However when no or little oxygen is present, what is the case in hypoxic tumors, less reactive oxygen species are formed and the irradiation is not as effective. It has been shown that a 3 fold higher radiation dose is required to kill the same amount of hypoxic cells as compared under normal oxygen concentrations. The concept of radiosensitization of hypoxic cells emerged when certain compounds were able to mimic oxygen and thus enhance radiation damage. The first compounds which demonstrated radiosensitization were nitrobenzenes, followed by nitrofurans and 2-nitroimidazoles, such as misonidazole (see e.g. WO02006102759). Although in experimental tumor models enhanced radiation damage was observed, most of the clinical trials using misonidazole were unable to demonstrate a significant improvement in radiation response, although benefit was seen in certain subgroups of patients (Overgaard, 1989). The most likely explanation is the fact that the misonidazole doses were too low, limited by the risk of neurotoxicity. Alternative, better radiosensitizing drugs, such as etanidazole and pimonidazole, were synthesized and tested, but clinical results did not result in a significant therapeutic benefit. Less toxic drugs, such as nimorazole, could theoretically achieve lower sensitizing ability compared with misonidazole, but due to it far lower toxicity, much higher, clinically relevant doses can be obtained. Only clinical studies in patients with supraglottic and pharyngeal carcinomas (DAHANCA 5) resulted in highly significant benefit in terms of improved loco-regional tumor control and disease-free survival (Overgaard et al, 1998). More specific targeting towards the hypoxic tumor cell using lower doses is therefore an important requisite for new compounds.

It now has surprisingly been found that the compounds of the invention, as represented by formula (1):

in which Z is Z1 represented by formula (2a):

or Z is Z2 represented by formula (2b): $(CH_2)_n CH2X$
or Z is Z3 represented by formula (2c):

R1 and R2 can be, each independently, H, alkyl, alkenyl, alkynyl, cycloalkyl, heterocyclic, aryl, cyano or halogen atom, R3, R4, R6 and R7 can be, each independently H, alkyl, alkenyl, alkynyl, cycloalkyl, heterocyclic, aryl, halogen atom, cyano, alkoxy, sulfonamide, sulfamate or sulfamide, R5 can be sulfonamide, sulfamate or sulfamide, X=sulfonamide, sulfamate or sulfamide, Y=O or S, and n=0, 1, 2, 3, 4 or 5, demonstrate not only a higher specificity for CA IX than any compound known in the art, but also have a much increased radiosensitizing effect. This is the more unexpected as the stereochemical orientation of the various active groups in the compounds of the invention is quite different from that of the compounds known in the art be it sulfonamides or nitroimidazoles. In other words, it is surprising that the radiosensitizing activity of the nitroimidazoles has been retained although the group now is part of a larger entity and the compounds are less neurotoxic.

Therefore the compounds of the invention have a significantly improved overall profile for treating solid tumours, such as tumours of the breast, brain, kidney, colorectal, lung, head and neck, bladder etc. compared to carbonic anhydrase inhibitors known in the art. Also other therapeutic fields such as treating eye disorders in particular, glaucoma, ocular hypertension, age-related macular degeneration, diabetic macular edema, diabetic retinopathy, hypertensive retinopathy and retinal vasculopathies, epilepsy, high-altitude disorders and neuromuscular diseases fall within the range of applications of the compounds of the invention.

Another finding is that the compounds of the invention also show an unexpected positive effect on radiosensitivity. Extracellular acidosis has been thought to be the result of excess production of lactic acid. However, glycolytic deficient cells (cells in which lactic acid production is hampered) result in tumors with a similar extent of extracellular acidosis, indicating other involved players aside lactic acid. Several studies have been shown that extracellular acidosis makes tumours less sensitive to irradiation treatment (Brizel et al, 2001; Quennet et al, 2006). Carbonic anhydrase inhibiting sulfonamides are able to reduce the extracellular acidosis in tumors and are therefore a possible tool to improve the sensitivity to irradiation of tumours. In addition, the fact that CA IX expression is limited in normal healthy tissue, while highly overexpressed in tumours, makes the carbonic anhydrase isozyme IX an attractive target within the concept.

On the other hand, hypoxic conditions in tumours make them less sensitive to the ionising radiation commonly used in radiotherapy (Thomlinson & Gray, 1955). Attracting the CA inhibitory compounds towards hypoxic cells, would greatly increase the possible therapeutic effect. This can be done using nitroimidazoles which are trapped in hypoxic cells after a two-fold electron reduction upon low oxygen conditions.

In other words, on the one hand there is a need to increase the anti-acidic, antitumorigenic effects and specificity of CA IX inhibiting sulf(on)amides and on the other hand there is a need to target specifically hypoxic cells using substituted nitroimidazoles to make compounds more suitable for radiosensitizing therapy. These needs are met by the present invention which provides multifunctional dual CAIX targeting drug compounds and preparations for the treatment of cancer in a patient in need thereof comprising compounds of formula 1a-c above.

Further objects of the present invention are also pharmaceutical compositions containing at least a compound of the present invention of formula (1a-c) together with non toxic adjuvants and/or carriers usually employed in the pharmaceutical field.

The invention will now be described in more detail below, with reference to the figures in which
FIG. 1 shows Scheme 1.

Figure 1:
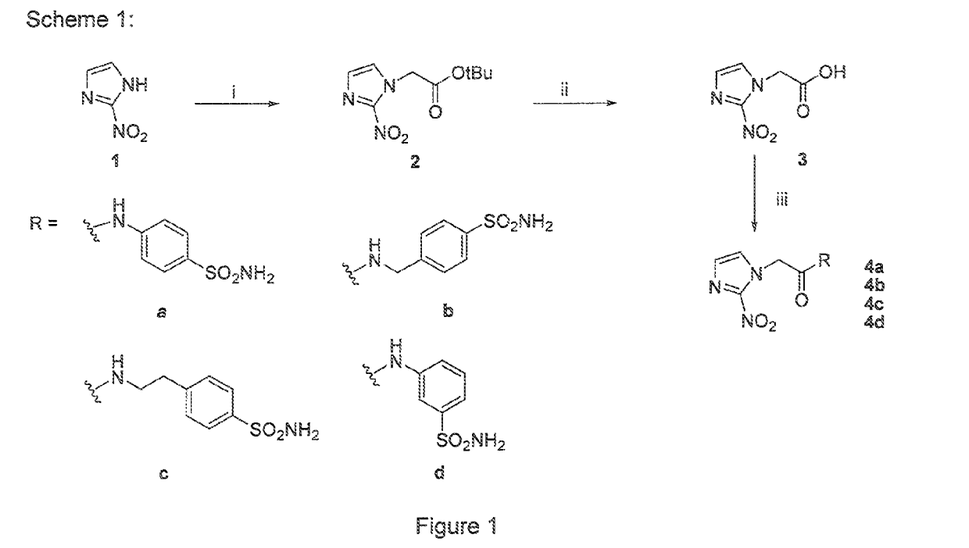
FIG. 1 shows the synthesis of compounds 4a-d.

Reagents and conditions: (i) 1 equiv. of 2-nitroimidazole, 1 equiv. of tert-butyl bromoacetate, 4 equiv. of potassium carbonate, MeCN, RT, 1 night: (ii) cocktail of trifluoroacetic acid/water/thioanisole 95/2.5/2.5 v/v, room temperature, 1 night; (iii) 1 equiv. of 4-dimethylaminopyridine (DMAP), 1 equiv. of 1-(3-dimethylaminopropyl)-3-ethylcarbodiimide hydrochloride (EDC), N,N-dimethylacetamide (DMA), room temperature, 2 days.

Figure 2:
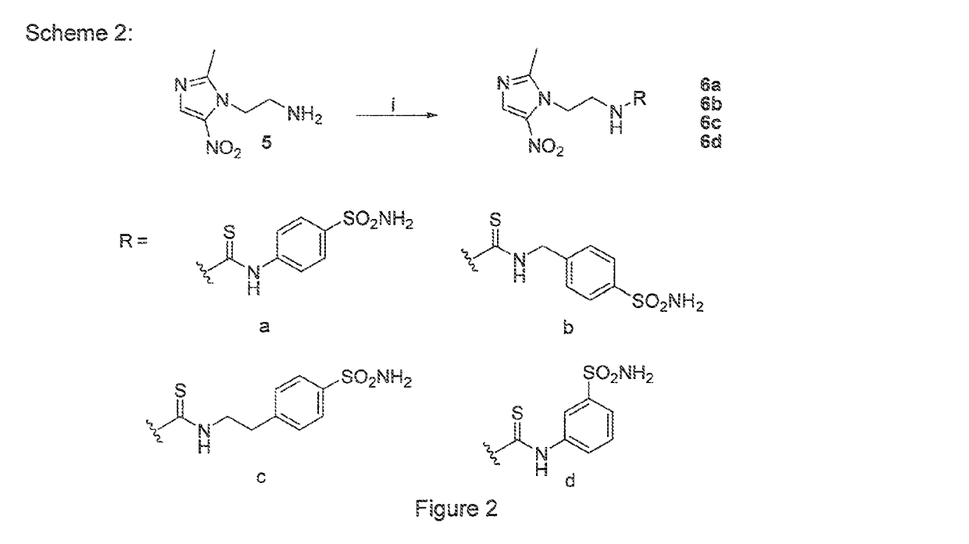
FIG. 2 shows the synthesis of compounds 6a-d.

FIG. 2 shows scheme 2:
Reagents and conditions: (i) 1 equiv. of 1-(2-aminoethyl)-2-methyl-5-nitroimidazole dihydrochloride monohydrate, 1 equiv. SCN-Ph-SO$_2$NH$_2$, 2 equiv. of triethylamine, MeCN, room temperature, 1 hour.

Figure 3:
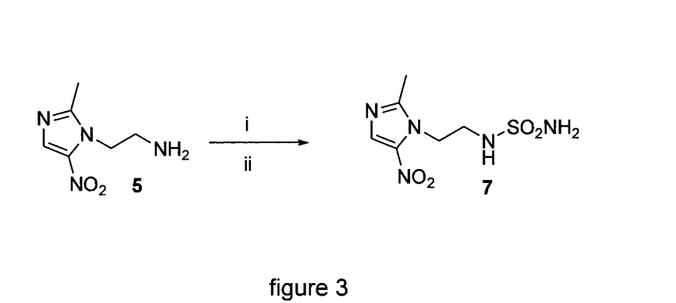
FIG. 3 shows a preferred compound (7) of the invention.

FIG. 3 shows the scheme of the preferred compound of the invention
Reagents and conditions: (i) 1 equiv. of 1-(2-aminoethyl)-2-methyl-5-nitroimidazole dihydrochloride monohydrate, 4 equiv. of triethylamine, 1 equiv. of chlorosulfonylisocyanate, 1 equiv. of tert-butanol, CH$_2$Cl$_2$, rt, 1 hour; (ii) trifluoroacetic acid/CH$_2$Cl$_2$ 7/3, rt, 6 hours.

Figure 4:
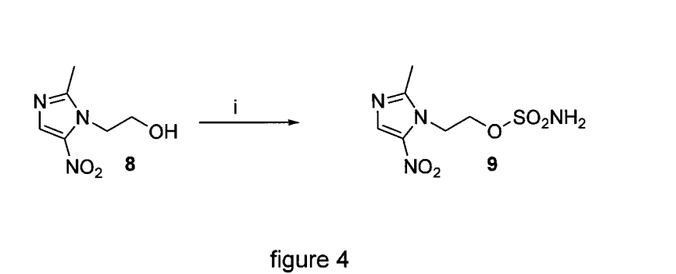
FIG. 4 shows another preferred compound (9) of the invention.

FIG. 4 shows the scheme of the second preferred compound of the invention
Reagents and conditions: (i) 1 equiv. of 2-methyl-5-nitro-1-imidazolylethanol, N,N-dimethylacetamide, 3 equiv. sulfamoyl chloride, rt, 1 night.

The compounds of the present invention can be synthesised according to the following procedures. All reagents and solvents were of commercial quality and used without further purification, unless otherwise specified. All reactions were carried out under an inert atmosphere of nitrogen. TLC analyses were performed on silica gel 60 F$_{254}$ plates (Merck Art. 1.05554). Spots were visualized under 254 nm UV illumination, or by ninhydrin solution spraying. Melting points were determined on a Büchi Melting Point 510 and are uncorrected. $^1$H and $^{13}$C NMR spectra were recorded on Bruker DRX-400 spectrometer using DMSO-d$_6$ as solvent and tetramethylsilane as internal standard. For $^1$H NMR spectra, chemical shifts are expressed in δ (ppm) downfield from tetramethylsilane, and coupling constants (J) are expressed in Hertz. Electron Ionization mass spectra were recorded in positive or negative mode on a Water MicroMass ZQ.

It is referred to the attached FIGS. 1 and 2.

tert-butyl-(2-nitro-imidazol-1-yl)acetate (2)

To a mixture of 2-nitroimidazole 1 (17.7 mmol, 1 equiv.) and anhydrous potassium carbonate (70.74 mmol, 4 equiv.) in 20 mL of acetonitrile is added dropwise a solution of tert-butylbromoacetate (17.7 mmol, 1 equiv.) in 10 ml of acetonitrile. The mixture is stirred one night at room temperature and concentrated under vacuum. The residue is purified by chromatography on silica gel using a mixture CH$_2$Cl$_2$/MeOH 95/5 as eluent to give the expected compound as white powder in 71% yield. mp 95-97° C.; $^1$H NMR (DMSO-d$_6$, 400 MHz) δ 1.46 (s, 9H), 4.99 (s, 2H), 7.06 (d, 1H, J=1.01 Hz), 7.17 (d, 1H, J=1.01 Hz). MS (ESI$^+$/ESI$^-$) m/z 226.15 [M−H]$^−$, 262.13 [M+Cl]$^−$, 250.20 [M+H]$^+$ (2-nitro-imidazol-1-yl)acetic acid (3)

Compound 2 (2.5 g) is dissolved in 20 mL of a cocktail of TFA, water, thioanisole 95-2.5-2.5 and stirred at room temperature for one night. The mixture is then concentrated under vacuum and co-evaporated several times with diethyl ether until formation of a powder. After filtration, the precipitate is washed with dichloromethane and acetonitrile to give quantitatively the expected product. Mp 143° C. (decomposition); $^1$H NMR (DMSO-d$_6$, 400 MHz) δ 5.21 (s, 2H), 7.21 (d, 1H, J=1.01 Hz), 7.64 (d, 1H, J=1.01 Hz). $^{13}$C (DMSO-d$_6$, 101 MHz) δ 50.65, 127.69, 128.44, 168.56, 168.57; MS (ESI$^+$/ESI$^-$) m/z 170.12 [M−H]$^−$, 341.05 [2M−H]$^−$, 194.14 [M+Na]$^+$.

General Procedure for the Preparation of Compounds (4a-d)

To a solution of compound 3 (1.17 mmol, 1 equiv.) in 8 mL of N,N-dimethylacetamide was added the aminoalkylbenzene sulfonamide (1.17 mmol, 1 equiv.), 4-dimethylaminopyridine (1.17 mmol, 1 equiv.) and 1-ethyl-3-(3-dimethylaminopropyl)carbodiimide (1.17 mmol, 1 equiv.). The mixture was stirred two days at room temperature, then diluted with ethyl acetate and washed three times with water. The organic layer was dried over anhydrous magnesium sulfate, filtrated and concentrated under vacuum. The residue was then purified by chromatography on silica gel using methylene chloride-methanol 98-2 v-v as eluent.

2-(2-nitro-imidazol-1-yl)-N-(4-sulfamoylphenyl)acetamide (4a, DH296)

Yield: 68%; mp 163-165° C.; $^1$H NMR (DMSO-d$_6$, 400 MHz) δ 5.36 (s, 2H), 7.24 (d, 1H, J=1.01 Hz), 7.28 (s, 2H), 7.67 (d, 1H, J=1.01 Hz), 7.70 (d, 2H, J=8.9 Hz), 7.77 (d, 2H, J=8.9 Hz), 10.7 (s, 1H); $^{13}$C (DMSO-d$_6$, 101 MHz) δ 52.20, 118.70, 126.81, 127.57, 128.84, 138.76, 141.18, 144.79, 165.02; MS (ESI⁺/ESI⁻) m/z 324.09 [M–H]⁻, 359.92 [M+Cl]⁻, 649.15 [2M–H]⁻, 685.01 [2M+Cl]⁻, 348.14 [M+Na]⁺.

2-(2-nitro-imidazol-1-yl)-N-(3-sulfamoylphenyl)acetamide (4b, DH304)

Yield: 79%; mp 195-197° C.; $^1$H NMR (DMSO-d$_6$, 400 MHz) δ 5.35 (s, 2H), 7.24 (d, 1H, J=1.01 Hz), 7.38 (s, 2H), 7.52 (m, 2H), 7.65 (m, 1H), 7.67 (d, 1H, J=1.01 Hz), 8.14 (s, 1H), 10.81 (s, 1H); $^{13}$C (DMSO-d$_6$, 101 MHz) δ 52.16, 116.10, 120.72, 121.92, 127.59, 128.86, 129.67, 138.67, 144.72, 164.87, 167.75; MS (ESI⁺/ESI⁻) m/z 324.24 [M–H]⁻, 360.18 [M+Cl]⁻, 685.13 [2M+Cl]⁻, 326.24 [M+H]⁺, 348.07 [M+Na]⁺, 364.17 [M+K]⁺, 673.18 [2M+Na].

2-(2-nitro-imidazol-1-yl)-N-(4-sulfamoylbenzyl)acetamide (4c, DH305)

Yield: 83%; mp 181-183° C.; $^1$H NMR (DMSO-d$_6$, 400 MHz) δ 4.37 (d, 2H, J=5.7 Hz), 5.22 (s, 2H), 7.18 (d, 1H, J=1.01 Hz), 7.35 (s, 2H), 7.43 (d, 2H, J=8.4 Hz), 7.67 (d, 1H, J=1.01 Hz), 7.76 (d, 2H, J=8.4 Hz), 9.15 (t, 1H, J=6.06 Hz); $^{13}$C (DMSO-d$_6$, 101 MHz) δ 41.81, 51.55, 106.87, 125.58, 127.39, 138.91, 142.66, 142.99, 156.82, 165.88; MS (ESI⁺/ESI⁻) m/z 338.15 [M–H]⁻, 374.22 [M+Cl]⁻, 713.16 [2M+Cl]⁻, 340.15 [M+H]⁺, 362.17 [M+Na]⁺.

2-(2-nitro-imidazol-1-yl)-N-[2-(4-sulfamoylphenyl)ethyl]acetamide (4d, DH302)

Yield: 89%; mp 139-141° C.; $^1$H NMR (DMSO-d$_6$, 400 MHz) δ 2.80 (t, 2H, J=6.9 Hz), 3.16 (m 2H), 5.07 (s, 2H), 7.18 (d, 1H, J=1.01 Hz), 7.30 (s, 2H), 7.40 (d, 2H, J=8.2 Hz), 7.61 (d, 1H, J=1.01 Hz), 7.74 (d, 2H, J=8.2 Hz), 8.46 (t, 1H, J=5.6 Hz); $^{13}$C (DMSO-d$_6$, 101 MHz) δ 34.59, 51.49, 125.64, 127.38, 128.74, 129.09, 142.05, 143.39, 144.87, 165.57; MS (ESI⁺/ESI⁻) m/z 352.19 [M–H]⁻, 388.07[M+Cl]⁻, 354.12 [M+H]⁺, 376.09 [M+Na]⁺, 729.21 [2M+Na]⁺.

General Procedure for the Preparation of Compounds (6a-d):

To a solution of the commercially available compound 5 (0.76 mmol, 1 equiv.) in 10 mL of acetonitrile, was added the corresponding isothiocyanate (0.76 mmol, 1 equiv.). The reaction was stirred for one hour at room temperature and then filtered. The filtrate was concentrated under vacuum, and the residue obtained purified by chromatography on silica gel using methylene chloride-methanol 95-5 as eluent.

N-(4-sulfamoylphenyl)-N-((2-aminoethyl)-2-methyl-5-nitroimidazolyl)thiourea (6a, DH307)

Yield: 72%; mp 186-188° C.; $^1$H NMR (DMSO-d$_6$, 400 MHz) δ 2.42 (s, 3H), 3.91 (m, 2H), 4.5 (t, 2H, J=5.68 Hz), 7.3 (s, 2H), 7.46 (d, 2H, J=8.7 Hz), 7.71 (d, 2H, J=8.7 Hz), 8.05 (s, 2H), 10.0 (s, 1H); $^{13}$C (DMSO-d$_6$, 101 MHz) δ 13.81, 42.87, 44.86, 122.46, 126.30, 133.19, 138.66, 139.14, 141.88, 151.35, 180.88; MS (ESI⁺/ESI⁻) m/z 385.17 [M+H]⁺, 407.07 [M+Na]⁺, 769.22 [2M+H]⁻, 383.21 [M–H]⁻, 419.18 [M+Cl]⁻, 767.16. [2M–H]⁻.

N-(3-sulfamoylphenyl)-N-((2-aminoethyl)-2-methyl-5-nitroimidazolyl)thiourea (6b, DH309)

Yield: 75%; mp 66-68° C.; $^1$H NMR (DMSO-d$_6$, 400 MHz) δ 2.43 (s, 3H), 3.91 (m, 2H), 4.49 (t, 2H, J=5.68 Hz), 7.39 (s, 2H), 7.51 (m, 1H), 7.55 (s, 0.1H), 7.57 (m, 1H), 7.81 (s, 1H, 1H), 7.93 (m, 1H), 8.04 (s, 1H), 9.94 (s, 1H); $^{13}$C (DMSO-d$_6$, 101 MHz) δ 13.81, 42.82, 44.99, 120.29, 121.39, 126.62, 129.09, 133.18, 138.65, 139.51, 144.35, 151.37, 181.28; MS (ESI⁺/ESI⁻) m/z 385.23[M+H]⁺, 406.94 [M+Na]⁺, 791.19 [2M+Na]⁺, 383.12 [M–H]⁻, 419.09 [M+Cl]⁻, 767.26 [2M–H]⁻.

N-(4-sulfamoylbenzyl)-N-((2-aminoethyl)-2-methyl-5-nitroimidazolyl)thiourea (6c, DH310)

Yield: 82%; mp 67-69° C.; $^1$H NMR (DMSO-d$_6$, 400 MHz) δ 2.37 (s, 3H), 2.87 (m, 2H), 4.43 (t, 2H, J=5.18 Hz), 4.70 (br s, 2H), 7.32 (s, 2H), 7.34 (d, 2H, J=8.4 Hz), 7.68 (s, 1H), 7.75 (d, 2H, J=8.4 Hz), 8.03 (s, 1H), 8.15 (s, 1H); $^{13}$C (DMSO-d$_6$, 101 MHz) δ 13.84, 30.64, 42.70, 45.44, 125.52, 127.23, 133.17, 138.61, 142.48, 151.41, 181.44; MS (ESI⁺/ESI⁻) m/z 399.23 [M+H]⁺, 421.16 [M+Na]⁺, 797.08 [2M+H]⁺, 819.26 [2M+Na]⁺, 397.10 [M–H]⁺, 433.09 [M+Cl]⁻, 795.33 [2M–H]⁻.

N-(4-sulfamoylphenylethyl)-N-((2-aminoethyl)-2-methyl-5-nitroimidazolyl)thiourea (6d; DH308)

Yield: 86%; mp 75-77° C.; $^1$H NMR (DMSO-d$_6$, 400 MHz) δ 2.35 (s, 3H), 2.83 (m, 2H), 3.62 (m, 2H), 3.82 (m, 2H), 4.41 (m, 2H), 7.31 (s, 2H), 7.37 (d, 2H, J=8.2 Hz), 7.52 (s, 1H), 7.63 (s, 1H), 7.74 (d, 2H, J=8.2 Hz), 8.03 (s, 1H); $^{13}$C (DMSO-d$_6$, 101 MHz) δ 13.78, 30.64, 45.4, 125.65, 129.05, 133.18, 138.54, 142.03, 143.45, 151.42, 180.83; MS (ESI⁺/ESI⁻) m/z 413.06 [M+H]⁺, 435.02 [M+Na]⁺, 825.09 [2M+H]⁺, 847.21 [2M+Na]⁺, 411.06 [M–H]⁺, 447.20 [M+Cl]⁻, 822.99 [2M–H]⁻, 859.26 [2M+Cl]⁻.

Preferred Compounds (7) and (9)

N-[2-(2-methyl-5-nitro-imidazol-1-yl)ethyl]sulfamide (7; DH348)

To a solution of 5 (3.83 mmol, 1 equiv.) and triethylamine (30.63 mmol, 4 equiv.) in 10 mL of methylene chloride was added a solution of chlorosulfonyl)isocyanate (4.59 mmol, 1.2 equiv), tert-butanol (4.59 mmol, 1.2 equiv.) in 2 mL of methylene chloride (prepared ab-initio). The mixture was stirred at room temperature for one hour, then diluted with ethyl acetate and washed with water. The organic layer was dried over anhydrous sodium sulfate, filtered and concentrated under vacuum. The residue was purified by chromatography on silica gel using methylene chloride-methanol 98-2 as eluent. This intermediate was then diluted in a solution of trifluoroacetic acid in methylene chloride (30% volume), and stirred at room temperature for 6 hours. The mixture was then concentrated under vacuum and co-evaporated several times with diethyl ether to give the expected sulfamide as a white powder. Overall Yield: 70%; mp 122° C.; $^1$H NMR (DMSO-d$_6$, 400 MHz) δ 2.52 (s, 3H), 3.26 (m, 2H), 4.37 (t, 2H, J=5.81 Hz), 6.65 (s, 2H), 6.86 (s, 1H), 8.1 (s, 1H); $^{13}$C (DMSO-d$_6$, 101 MHz) δ 14.03, 41.8, 46.0, 132.68, 138.26, 151.65; MS (ESI⁺/ESI⁻) m/z 250.19 [M+H]⁺, 272.34 [M+Na]⁺, 499.32 [2M+H]⁺, 249.09 [M–H]⁻, 284.12 [M+Cl]⁻, 533.14 [2M+Cl]⁻.

N-[2-(2-methyl-5-nitro-imidazol-1-yl)ethyl]sulfamate (9; DH338)

To a solution of the commercially available compound 8 (1.75 mmol, 1 equiv.) in N,N-dimethylacetamide, was added sulfamoyl chloride (5.25 mmol, 3 equiv.). The mixture was stirred at room temperature for one night, then diluted with ethyl acetate, and washed three times with water. The organic layer was dried over anhydrous magnesium sulphate, filtered and concentrated under vacuum. The residue was purified by chromatography on silica gel using methylene chloride-methanol 9-1 as eluent. Yield: 81%; mp 166-168° C.; $^1$H NMR (DMSO-$d_6$, 400 MHz) δ 2.45 (s, 3H), 4.35 (t, 2H, J=5.05 Hz), 4.61 (t, 2H, J=5.05 Hz), 7.57 (s, 2H), 8.06 (s, 1H); $^{13}$C (DMSO-$d_6$, 101 MHz) δ 14.04, 44.98, 57.21, 133.10, 138.32, 151.82; MS (ESI$^+$/ESI$^-$) m/z 250.3 [M+H]$^+$, 272.32 [M+Na]$^+$, 521.30 [2M+Na]$^+$, 770.16 [3M+Na]$^+$.

In Vitro Experiments.

The compounds of the invention were tested for their effects on CA inhibition and the resulting effect on extracellular acidosis using classical chemistry and biology assays.

CA Inhibiting Activity.

The compounds of the invention were tested on their inhibitory activity on carbonic anhydrase in the following experiment:

The inhibition constants (K) the compounds for four CA isozymes, CA I, II, IX and XII were determined. An Applied Photophysics (Oxford, UK) stopped-flow instrument has been used for assaying the CA-catalyzed $CO_2$ hydration activity (Khalifah, 1971). Phenol red (at a concentration of 0.2 mM) has been used as indicator, working at the absorbance maximum of 557 nm, with 10 mM Hepes (pH 7.5) as buffer, 0.1 M $Na_2SO_4$ (for maintaining constant the ionic strength), following the CA-catalyzed $CO_2$ hydration reaction for a period of 10-100 s. The $CO_2$ concentrations ranged from 1.7 to 17 mM for the determination of the kinetic parameters and inhibition constants. For each inhibitor at least six traces of the initial 5-10% of the reaction have been used for determining the initial velocity. The uncatalyzed rates were determined in the same manner and subtracted from the total observed rates. Stock solutions of inhibitor (1 mM) were prepared in distilled-deionized water with 10-20% (v/v) DMSO (which is not inhibitory at these concentrations) and dilutions up to 0.1 nM were done thereafter with distilled-deionized water. Inhibitor and enzyme solutions were preincubated together for 15 min at room temperature prior to assay, in order to allow for the formation of CA IX-inhibitor complex. The inhibition constants were obtained by non-linear last-squares methods using PRISM 3 and represent the mean from at least three different determinations.

The results are listed in table 1 below.

TABLE 1

| Compounds | | $K_I$ (nM) | | | |
|---|---|---|---|---|---|
| | | hCA I | hCA II | hCA IX | hCA XII |
| 9 | (DH 338) | 4435 | 33.8 | 8.3 | 8.9 |
| 7 | (DH 348) | 9576 | 10.1 | 20.4 | 8.1 |
| 6a | (DH307) | 105 | 5.5 | 7.3 | 8.0 |
| 6d | (DH308) | 84 | 6.6 | 7.8 | 7.6 |
| 6b | (DH309) | 483 | 7.4 | 7.2 | 7.7 |
| 6c | (DH310) | 79 | 2.9 | 8.3 | 8.5 |
| 4a | (DH296) | 3203 | 330 | 70 | 64 |
| 4d | (DH302) | 101 | 3.8 | 7.3 | 8.0 |
| 4b | (DH304) | 107 | 37 | 7.9 | 8.1 |
| 4c | (DH305) | 79 | 4.8 | 8.0 | 6.7 |

Acidosis.

The effects of compounds of the invention on acidosis in tumor cells was measured in the following experiment.

Aim of the in vitro experiments was to assess the efficacy of 4 compounds (7, 9, 6a and 6c) in reducing the extracellular acidification upon hypoxia.

Figure 5A:
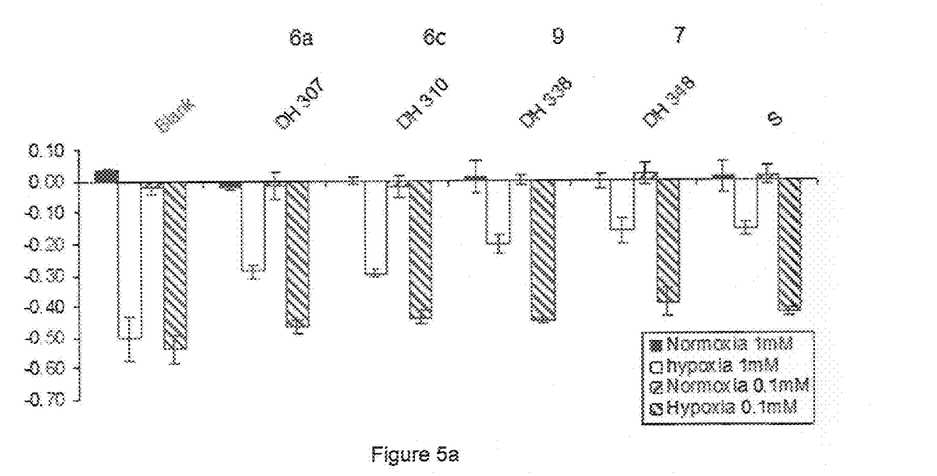
FIG. 5a-b; shows the effect of compounds (6a, 6c, 7 and 9) of the invention on acidosis in an in vitro tumor cell culture model.
Figure 5B:
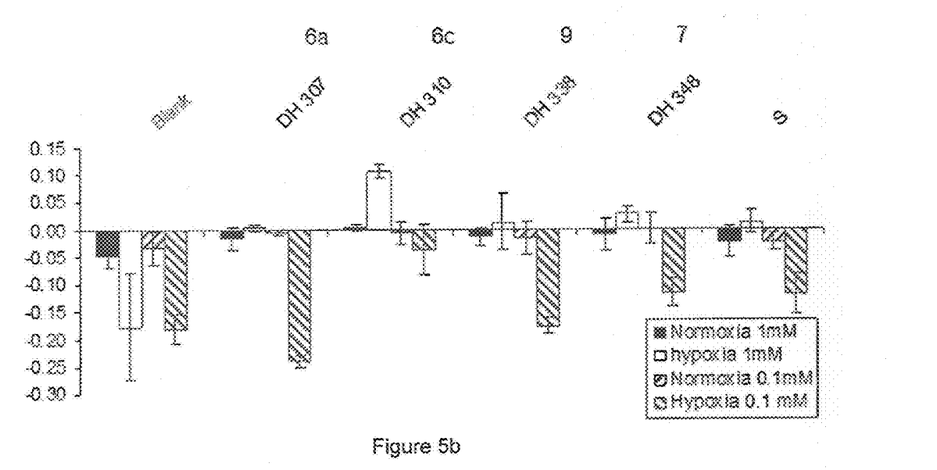
Figure 6A:
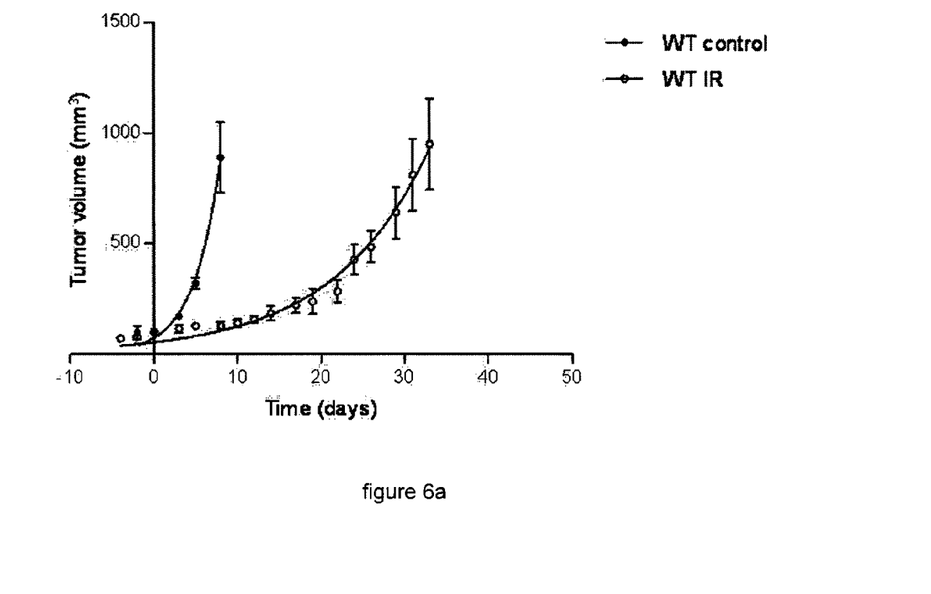
FIG. 6a-k shows the effect of compounds of the invention in combination with chemotherapeutic agents or radiation in an in vivo tumor model.
Figure 6B:
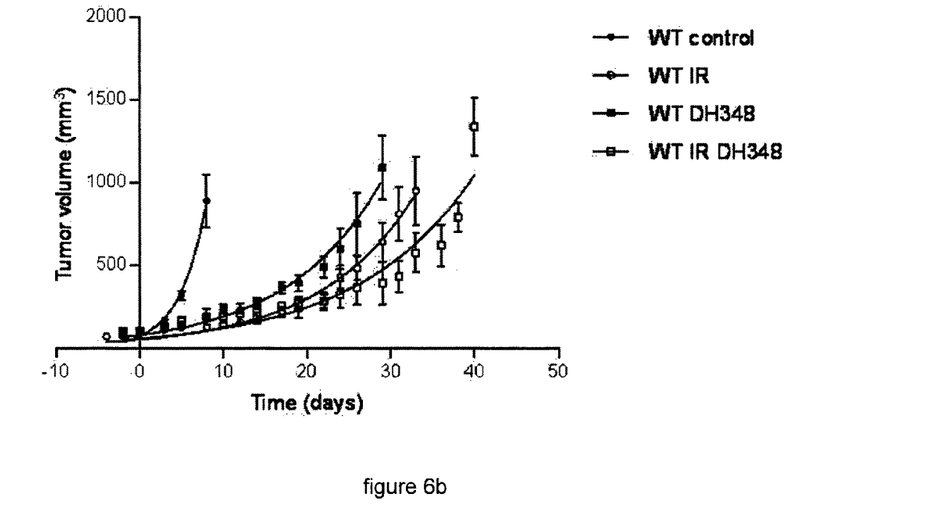
Figure 6C:
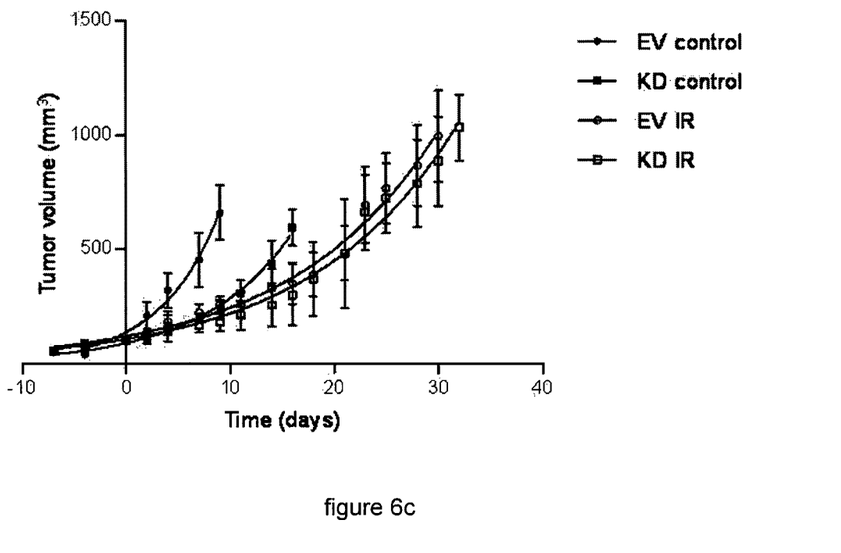
Figure 6D:
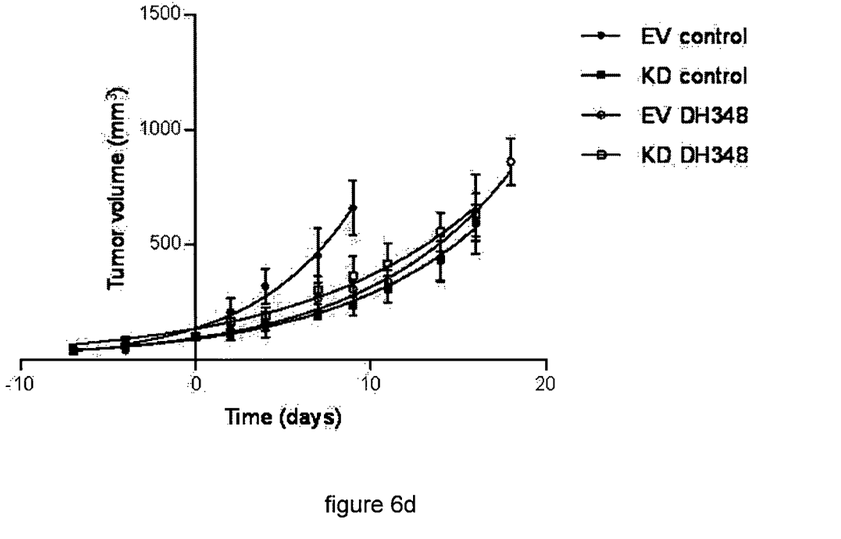
Figure 6E:
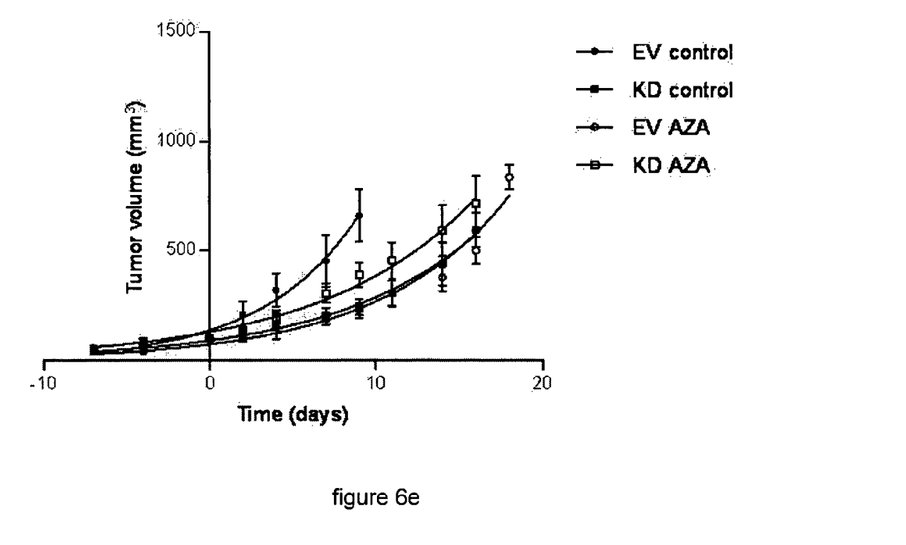
Figure 6F:
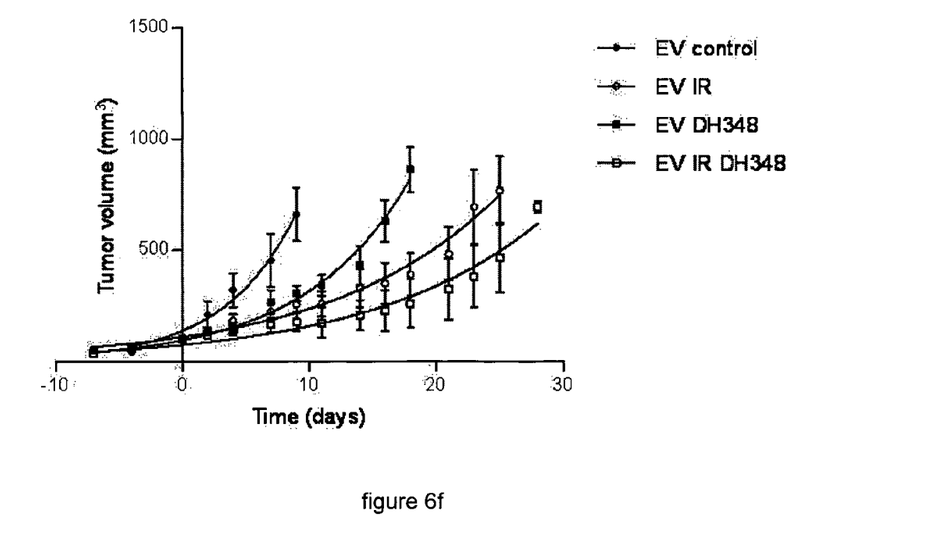
Figure 6G:
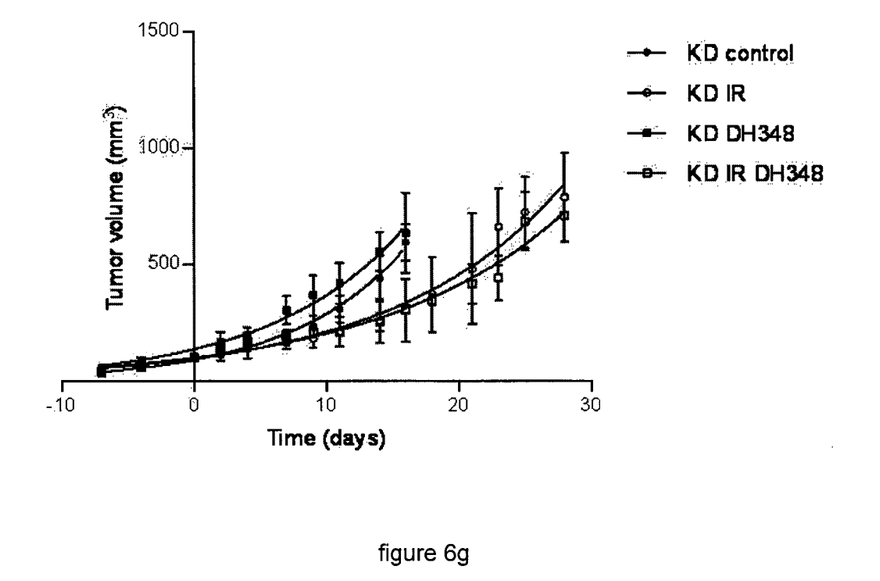
Figure 6H:
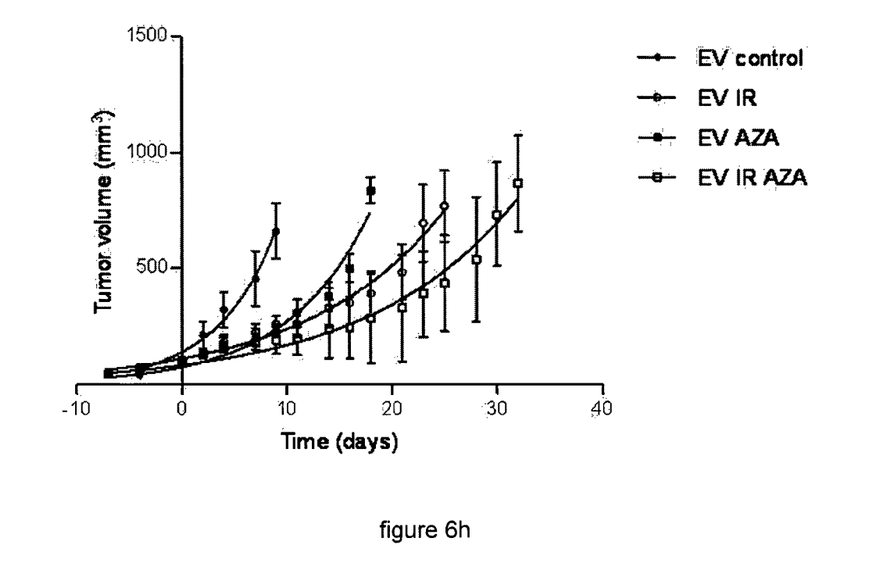
Figure 6I:
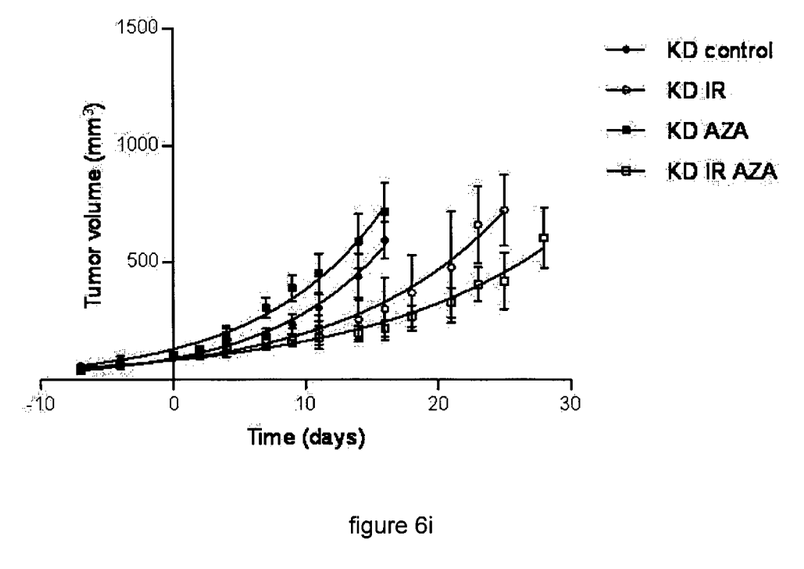
Figure 6J:
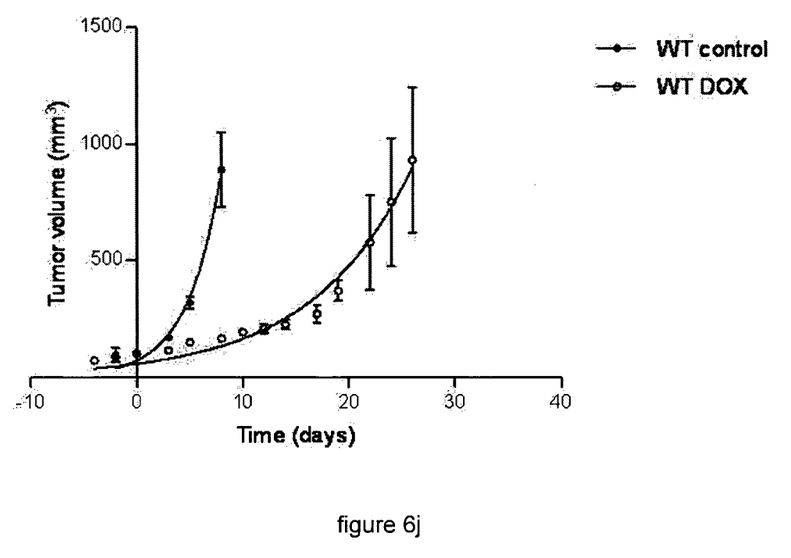
Figure 6K:
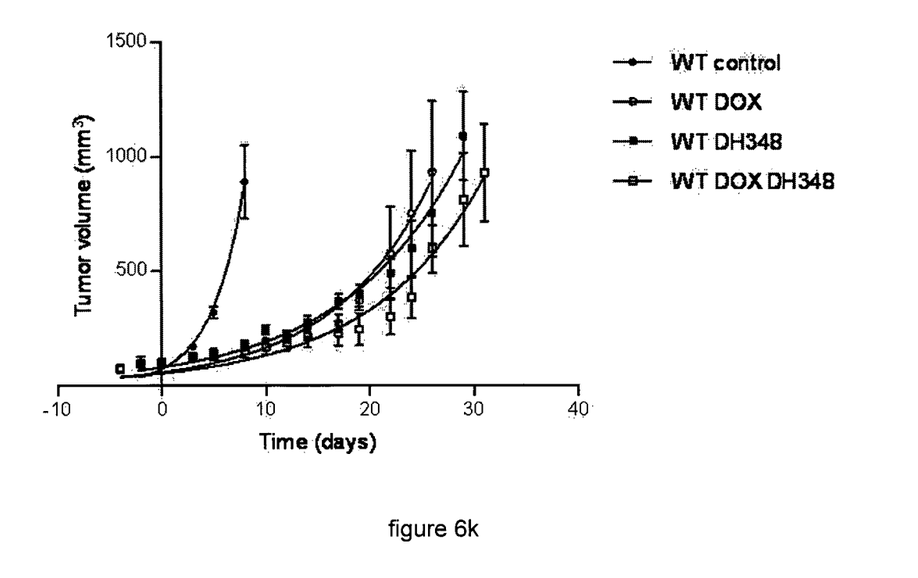
Figure 7:
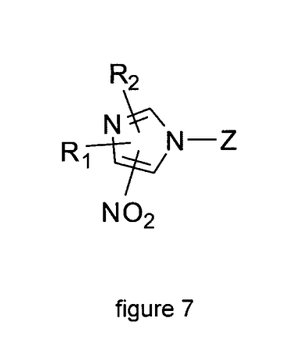
FIG. 7 depicts formula (1) according to the invention.

The experiment was set up as previously described (Dubois et al, 2007). A colorectal (HT-29) (FIG. 5a) and a cervical (HeLa) (FIG. 5b) carcinoma cell line were tested in normoxic (ambient oxygen concentration) and hypoxic (0.2% oxygen) conditions. HT-29 cells are known to be constitutive hypoxia inducible CA IX (CA IX expression under normoxia and increased CA IX expression upon hypoxia) expressing cells. Therefore, compounds were added after 1 h of hypoxic exposure (to ensure active CA IX) and incubation was done for another 23 h (total of 24 h hypoxia). HeLa cells are hypoxia inducible (at lower density) CA IX expressing cells. Therefore, HeLa were first incubated for 24 h hypoxia to ensure CA IX expression in the first place (time point assessed in time series experiments). Afterwards, compounds were added and cells were incubated for another 24 h.

Experiments were performed in triplicate for each condition. The described conditions were done both for HT-29 and HeLa under normoxic and hypoxic conditions.

Following conditions were assessed:
Blank 1 mM or 0.1 mM (no addition of compound, only DMSO/PBS)
DH307 1 mM or 0.1 mM
DH310 1 mM or 0.1 mM
DH338 1 mM or 0.1 mM
DH348 1 mM or 0.1 mM
S=AEBS (4-(2-aminoethylbenzenesulfonamide); Sigma) 1 mM or 0.1 mM (known to reduce extracellular pH as described by (Svastova et al, 2004))

Cells were seeded in 6 cm dishes (HT-29: 10e6; HeLa: 4×10$^5$: to compensate for cell size) in 5 ml of DMEM supplemented with 10% FCS. The day after, medium was replaced by 3.6 ml of freshly prepared DMEM/FCS 10%, from which the pH was measured=pH at incubation), after which dishes were placed in the hypoxic chamber (normoxic dishes remained at ambient air in the incubator: 37° C., 95% humidity, 5% $CO_2$). Compounds were added (1 h for HT-29 or 24 h for HeLa after start hypoxic exposure) to have a final concentration of 1 mM or 0.1 mM, by adding 400 µl to the dishes, starting from a 10 or 1 mM stock (DMSO final concentration 0.1%). Blanc controls received DMSO/PBS without compound. pH of the medium was measured after 24 h (HT-29) or 48 h (HeLa) inside the hypoxic chamber after calibration of the electrode to reduced oxygen concentrations. Delta pH (pH at end hypoxic exposure−pH of replacement medium before incubation) were calculated and shown in the graph of FIGS. 5a and 5b.

The important results are described below:
Hypoxia results into an extracellular acidification. The medium is more acid in blank conditions upon hypoxia compared with normoxia.
The control compound (S) effectively reduced the extracellular acidification upon hypoxia at 1 mM concentration (less at 0.1 mM) for both cell lines. No effect was seen upon normoxic exposure
All compounds were able to reduce the extracellular acidification. For HT-29 cells, DH348 (compound 7) and DH338 (compound 9) give the best results (1 mM). At 0.1 mM DH348 gives an additional reduction compared with the other compounds. For HeLa, all compounds effectively reduced the extracellular acidification. DH310 even made the medium alkaline (1 mM) and also 0.1 mM caused a strong reduction. Since this effect was not seen in HT-29, interpretation should be done carefully. DH348 demonstrated the best results in HeLa, and confirms the obtained data for HT-29.

In Vivo Experiments.

Aim of these experiments was to assess the in vivo therapeutic effect of DH348 in combination with conventional treatment modalities such as radiotherapy and chemotherapy. We hypothesize that blocking CA IX may both decrease extracellular acidosis, and thus increase the effect of irradiation, as well as increase the uptake of the weak base doxorubicin, and therefore its therapeutic effect. Furthermore, a clinically approved sulfonamide Acetazolamide (AZA)—a known general carbonic anhydrase inhibitor (meaning no preference for one CA)—was used to prove the CA IX specificity of the investigated compounds.

Two experimental setups were used. The first experiments were carried out on parental HT-29 xenografts. The second were done on HT-29 xenografts harbouring a knock-down for CA IX. A shRNA construct against CA IX was introduced in the HT-29 cells using the pRETRO-super vector. After selection and screening, cells with a 95% efficient knock-down for CA IX were selected and designated KO cells. As a control, a scrambled shRNA construct was used and those cells were designated EV cells. These cells still demonstrate CA IX mRNA and protein expression. Tumor xenografts were produced by injecting the colorectal carcinoma cells (1.5 10e6) subcutaneously into the lateral flank of NMRI-nu mice (28-32 g). Tumor growth was monitored 3×/week by measuring the tumor dimensions in 3 orthogonal directions. Measurements were corrected for skin thickness (−0.5 mm) and tumor volumes were calculated using the formula A×B×C×pi/6, were A, B and C represent the orthogonal diameters. At an average tumor volume of 250 mm$^3$, DH348 was injected intravenously (5×5 mg/kg intravenously) using the lateral tail vein. At day 3 animals were anaesthetized using Sodium Pentobarbital (Nembutal, 0.1 ml/100 g body weight) and positioned in the irradiation field using a custom-built jig and subjected to irradiation with a single dose of 10 Gy (15 meV electron beam) using a linear accelerator (Siemens). Another group of animals started at day 3 with doxorubicin treatment (5 mg/kg i.v. 1×/week for 3 weeks). Tumor growth and potential treatment toxicity was monitored (3×/week), by daily evaluation of the body weight. When tumors reached four times the treatment starting volume, animals were sacrificed and tumors excised for further histopathological evaluation. In summary the treatment groups are arranged as follows, with the results presented in the figures:

6a: HT-29 parental tumors (WT): effect of irradiation 10 Gy alone compared to no treatment (controls)
6b: HT-29 parental tumors (WT): effect of combination treatment (DH348+irradiation 10Gy) compared with DH348, irradiation or no treatment
6c: Effect of irradiation 10 Gy alone compared to no treatment on HT-29 shscrambled (EV) and shCA IX (KD) tumors
6d: Effect of DH348 treatment compared to no treatment on EV and KD tumors
6e: Effect of AZA treatment compared to no treatment on EV and KD tumors
6f: Effect of combination treatment with DH348 and irradiation 10 Gy compared to the single treatment modalities on EV tumors
6g: Effect of combination treatment with DH348 and irradiation 10 Gy compared to the single treatment modalities on KD tumors
6h: Effect of combination treatment with AZA and irradiation 10 Gy compared to the single treatment modalities on EV tumors
6i: Effect of combination treatment with AZA and irradiation 10 Gy compared to the single treatment modalities on KD tumors
6j: HT-29 parental tumors (WT): effect of doxorubicin treatment compared to no treatment (controls)
6k: HT-29 parental tumors (WT): effect of combination treatment (DH348+doxorubicin) compared with the single treatment modalities The tumor growth curves are shown in FIGS. 6a-6d. Tumor volumes are normalized to start treatment=100 mm$^3$). No significant treatment toxicity was observed as monitored by total body weight changes during treatment. Treatment with the compound of this invention results in a growth delay compared with no treatment. When combined with conventional clinically available treatment schedules, it results in a sensitization for radiotherapy and to a smaller extent for chemotherapy. This is indicated by the enhanced growth delay for the combination treatment, compared with the individual treatment arms. Furthermore, we have demonstrated similar results for the parental and scrambled shRNA bearing tumors. More important, we have shown a specific effect of the compounds on CA IX, since (1) the compound had no therapeutic effect on the CA IX shRNA (KD) tumors and (2) no enhanced growth delay was observed when combined with irradiation compared with irradiation alone. The specificity of the compound for CA IX was further confirmed by evaluation of the general CA inhibitor AZA, which demonstrated also an effect on the KD tumors. Since several other CA isozymes then CA IX are present in healthy tissues and AZA has inhibitory properties against those, normal tissue toxicity in prolonged treatments can be expected, a phenomenon what will be greatly reduced using the CA IX specific compounds of this invention.

Pharmaceutical Preparations.

The daily dose of active ingredient can be administered to a host in a single dose or it can be an effective amount divided into several smaller doses that are administered throughout the day. The pharmacotherapeutic regimen for treating the aforementioned diseases with a compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state. The compounds of the invention may be administered orally, parenterally, rectally or topically, by inhalation spray o aerosol, in dosage unit formulations containing conventional non-toxic pharmaceutically acceptable carriers, adjuvants and vehicles as desired. Topical preparations can be administered as solutions, suspensions or emulsions (dispersions) in an acceptable vehicle.

Topical administration may also involve the use of transdermal administration such as transdermal patches or iontophoresis devices. The term "parenteral" as used herein includes subcutaneous injections, intravenous, intramuscular, intrasternal injection or infusion techniques. Injectable preparations, for example, sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent o solvent. Among the acceptable vehicles and solvents are water, Ringer's solution and isotonic sodium chloride solution.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert compound such as sucrose, lactose or starch. Such dosage forms may also comprise, as in normal practice, additional substances, e.g. lubricating agents such as magnesium stearate. In the case of capsules, tablets and pills, the dosage forms may also comprise buffering agents. Tablets and pills can additionally be prepared with enteric coatings. Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, emulsifying and suspending agents, and sweetening, flavouring and the like.

It is further contemplated that the compounds of the present invention can be used with other medicaments known to be useful in the treatment of carcinomas.

The above examples are only to be considered as an illustration of the invention and do not limit the scope of the invention in any way. Hence, obvious variations and variants of the invention will be apparent to one skilled in the art.

REFERENCES

Brizel D M, Schroeder T, Scher R L, Walenta S, Clough R W, Dewhirst M W, Mueller-Klieser W (2001) Elevated tumor lactate concentrations predict for an increased risk of metastases in head-and-neck cancer. *Int J Radiat Oncol Biol Phys* 51: 349-53

Dubois L, Douma K, Supuran C T, Chiu R K, van Zandvoort M A, Pastorekova S, Scozzafava A, Wouters B G, Lambin P (2007) Imaging the hypoxia surrogate marker CA IX requires expression and catalytic activity for binding fluorescent sulfonamide inhibitors. *Radiother Oncol* 83: 367-73

Khalifah R G (1971) The carbon dioxide hydration activity of carbonic anhydrase. I. Stop-flow kinetic studies on the native human isoenzymes B and C. *J Biol Chem* 246: 2561-73

Melillo G (2006) Inhibiting hypoxia-inducible factor 1 for cancer therapy. *Mol Cancer Res* 4: 601-5

Overgaard J (1989) Sensitization of hypoxic tumour cells—clinical experience. *Int J Radiat Biol* 56: 801-11

Overgaard J, Hansen H S, Overgaard M, Bastholt L, Berthelsen A, Specht L, Lindelov B, Jorgensen K (1998) A randomized double-blind phase III study of nimorazole as a hypoxic radiosensitizer of primary radiotherapy in supraglottic larynx and pharynx carcinoma. Results of the Danish Head and Neck Cancer Study (DAHANCA) Protocol 5-85. *Radiother Oncol* 46: 135-46

Pastorekova S, Zavadova Z, Kostal M, Babusikova O, Zavada J (1992) A novel quasi-viral agent, MaTu, is a two-component system. *Virology* 187: 620-6

Quennet V, Yaromina A, Zips D, Rosner A, Walenta S, Baumann M, Mueller-Klieser W (2006) Tumor lactate content predicts for response to fractionated irradiation of human squamous cell carcinomas in nude mice. *Radiother Oncol* 81: 130-5

Supuran C T (2008) Carbonic anhydrases: novel therapeutic applications for inhibitors and activators. *Nat Rev Drug Discov* 7: 168-81

Svastova E, Hulikova A, Rafajova M, Zat'ovicova M, Gibadulinova A, Casini A, Cecchi A, Scozzafava A, Supuran C T, Pastorek J, Pastorekova S (2004) Hypoxia activates the capacity of tumor-associated carbonic anhydrase IX to acidify extracellular pH. *FEBS Lett* 577: 439-45

Thomlinson R H, Gray L H (1955) The histological structure of some human lung cancers and the possible implications for radiotherapy. *Br J Cancer* 9: 539-49

Winum J Y, Scozzafava A, Montero J L, Supuran C T (2009) Inhibition of carbonic anhydrase IX: a new strategy against cancer. *Anticancer Agents Med Chem* 9: 693-702

The invention claimed is:

1. A compound of formula (1), wherein Z is $Z_1$ with formula (2a):

or Z is $Z_2$ with formula (2b): $(CH_2)nCH_2X$, where X=sulfamate or sulfamide; or or $Z_2$ is of the formula: $(CH_2)nCH_2$—$SO_2NH_2$;

or Z is $Z_3$ with formula (2c):

wherein $R_1$ and $R_2$ are, each independently, H, alkyl, alkenyl, alkynyl, cycloalkyl, heterocyclic, aryl, cyano or halogen atom;

$R_3$, $R_4$, $R_6$ and $R_7$ are, each independently H, alkyl, alkenyl, alkynyl, cycloalkyl, heterocyclic, aryl, halogen atom, cyano, alkoxy, sulfonamide, sulfamate or sulfamide;

$R_5$ is sulfonamide, sulfamate or sulfamide;

Y=O or S; and n=0, 1, 2, 3, 4 or 5 and where if n=0, $R_2$=2-$CH_3$, Z=$Z_1$, $R_3$=$R_4$=$R_6$=$R_7$=H and $R_5$=$SO_2NH_2$, then the $NO_2$ is not on position 4, or a pharmaceutically acceptable salt thereof.

2. A compound of formula (1), wherein the compound is a compound of formula (3a)

a compound of formula (3b)

wherein X=sulfamate or sulfamide; or X is —SO$_2$NH$_2$; or a compound of formula (3c)

wherein $R_1$ and $R_2$ are, each independently, H, alkyl, alkenyl, alkynyl, cycloalkyl, heterocyclic, aryl, cyano or halogen atom;

$R_3$, $R_4$, $R_6$ and $R_7$ are, each independently H, alkyl, alkenyl, alkynyl, cycloalkyl, heterocyclic, aryl, halogen atom, cyano, alkoxy, sulfonamide, sulfamate or sulfamide;

$R_5$ is sulfonamide, sulfamate or sulfamide;

Y=O or S; and n=0, 1, 2, 3, 4 or 5, or a pharmaceutically acceptable salt thereof.

3. The compound or salt according to claim 1 wherein $R_1$ and $R_2$ are, each independently, H or CH$_3$.

4. The compound or salt according to claim 1 wherein $R_1$=$R_2$=H.

5. The compound or salt according to claim 1 wherein $R_3$=$R_4$=$R_7$.

6. The compound or salt according to claim 1 wherein $R_3$=$R_4$=$R_7$=H.

7. The compound or salt according to claim 1 wherein $R_5$ or $R_6$ is sulfonamide.

8. The compound or salt according to claim 1 wherein n=0, 1 or 2.

9. The compound or salt according to claim 1 wherein $R_1$=H and $R_2$=CH$_3$.

10. The compound or salt according to claim 1 wherein n=1.

11. The compound or salt according to claim 1 wherein Z is $Z_2$ with formula (2b), wherein X is sulfamate or sulfamide.

12. The compound or salt according to claim 1 wherein Y=S.

13. The pharmaceutical composition comprising a compound or salt of claim 1 and a pharmaceutically acceptable carrier.

* * * * *